US00RE50013E

(19) United States
(12) Reissued Patent
McEwen et al.

(10) Patent Number: US RE50,013 E
(45) Date of Reissued Patent: Jun. 18, 2024

(54) TOURNIQUET SYSTEM FOR PERSONALIZED RESTRICTION OF BLOOD FLOW

(71) Applicant: Western Clinical Engineering Ltd., Vancouver (CA)

(72) Inventors: James A. McEwen, Vancouver (CA); Michael Jameson, North Vancouver (CA); Jeswin Jeyasurya, Vancouver (CA); Kenneth L. Glinz, Richmond (CA)

(73) Assignee: Western Clinical Engineering Ltd., Vancouver (CA)

(21) Appl. No.: 17/735,993

(22) Filed: May 3, 2022

Related U.S. Patent Documents

Reissue of:
(64) Patent No.: 10,646,232
Issued: May 12, 2020
Appl. No.: 15/318,335
PCT Filed: May 20, 2015
PCT No.: PCT/CA2015/050458
§ 371 (c)(1),
(2) Date: Dec. 12, 2016
PCT Pub. No.: WO2016/011538
PCT Pub. Date: Jan. 28, 2016

U.S. Applications:
(60) Provisional application No. 62/029,288, filed on Jul. 25, 2014.

(51) Int. Cl.
*A61B 17/135* (2006.01)

(52) U.S. Cl.
CPC ..... *A61B 17/1355* (2013.01)

(58) Field of Classification Search
CPC . A61B 17/135; A61B 17/1355; A61B 17/132; A61B 17/1325; A61B 5/02233;
(Continued)

(56) References Cited

U.S. PATENT DOCUMENTS 2,943,859 A 7/1960 Koski et al.
3,906,937 A 9/1975 Aronson
(Continued)

FOREIGN PATENT DOCUMENTS

EP 0136279 4/1985
EP 2123218 11/2009
(Continued)

OTHER PUBLICATIONS

Datasheet for the Vena Pro (2015) (downloaded May 3, 2022).
(Continued)

*Primary Examiner* — Beverly M Flanagan
(74) *Attorney, Agent, or Firm* — Klarquist Sparkman, LLP

(57) ABSTRACT

Disclosed is a system and method for regulating tourniquet cuff pressure to restrict blood flow penetration past the cuff based on a personalized restrictive pressure (PRP). The system includes mechanisms for estimating a limb occlusion pressure (LOP) by determining a minimum pressure at which arterial blood penetration past an applied tourniquet cuff is stopped and measuring a pulsation characteristic associated with the LOP. Thereafter, the system establishes a PRP by determining a second pressure that restricts but does not stop arterial blood penetration past the cuff and that corresponds to a second pulsation characteristic differing by a percentage from the pulsation characteristic associated with the LOP. During a limb-activity time period, the system maintains pressure in the applied tourniquet cuff near the PRP, thereby restricting but not stopping arterial blood penetration past the cuff during the activity time period.

14 Claims, 5 Drawing Sheets

(58) Field of Classification Search
CPC ... A61B 5/022; A61B 5/0225; A61B 5/02255; A61B 5/02208; A61B 5/02216
See application file for complete search history.

(56) References Cited

U.S. PATENT DOCUMENTS

| | | | | |
|---|---|---|---|---|
| 4,572,205 | A | 2/1986 | Sjönell | |
| 4,621,383 | A | 11/1986 | Gendala | |
| 4,637,394 | A | 1/1987 | Racz et al. | |
| 4,667,672 | A | 5/1987 | Romanowski | |
| 4,928,701 | A | 5/1990 | Harada et al. | |
| 5,022,387 | A | 6/1991 | Hasty | |
| 5,263,473 | A | 11/1993 | McWhorter | |
| 5,584,853 | A | 12/1996 | McEwen | |
| 5,733,304 | A | 3/1998 | Spence | |
| 5,853,005 | A | 12/1998 | Scanlon | |
| 5,931,853 | A * | 8/1999 | McEwen et al. .. | A61B 17/1355 606/203 |
| 6,149,618 | A | 11/2000 | Sato | |
| 6,447,467 | B1 | 6/2002 | Barak | |
| 6,478,757 | B1 | 11/2002 | Barak | |
| 6,605,103 | B2 | 8/2003 | Hovanes et al. | |
| 6,846,295 | B1 | 1/2005 | Ben-Nun | |
| 7,063,676 | B2 | 6/2006 | Barak et al. | |
| 7,413,527 | B2 | 8/2008 | Sato | |
| 7,455,630 | B2 | 11/2008 | Sato | |
| 7,654,964 | B1 * | 2/2010 | Kroll ..... | A61B 5/02028 600/481 |
| 7,780,698 | B2 | 8/2010 | McEwen et al. | |
| 8,021,283 | B2 | 9/2011 | Sato et al. | |
| 8,182,403 | B2 | 5/2012 | Sato | |
| 8,273,114 | B2 | 9/2012 | Wasowski | |
| 8,328,693 | B2 | 12/2012 | Sato | |
| 8,366,740 | B2 | 2/2013 | McEwen et al. | |
| 8,419,666 | B2 | 4/2013 | Liu et al. | |
| 8,425,426 | B2 | 4/2013 | McEwen et al. | |
| 8,506,508 | B2 | 8/2013 | Avitable et al. | |
| 8,597,194 | B2 | 12/2013 | Barak | |
| 8,721,575 | B2 | 5/2014 | Brown | |
| 8,740,828 | B2 | 6/2014 | Brown et al. | |
| 8,784,346 | B2 | 7/2014 | Barak et al. | |
| 8,992,397 | B2 | 3/2015 | Sato | |
| 9,107,793 | B2 | 8/2015 | Avitable et al. | |
| 9,114,052 | B2 | 8/2015 | Avitable et al. | |
| 9,301,701 | B2 | 4/2016 | McEwen et al. | |
| 9,386,928 | B2 | 7/2016 | Quinn et al. | |
| 9,387,146 | B2 | 7/2016 | Avitable et al. | |
| 9,788,738 | B2 | 10/2017 | Barak et al. | |
| 9,872,812 | B2 * | 1/2018 | Malhi ..... | A61H 9/0078 |
| 9,877,733 | B1 | 1/2018 | Jafary | |
| 10,245,458 | B2 | 4/2019 | Sato | |
| 10,646,231 | B2 | 5/2020 | McEwen et al. | |
| 10,646,232 | B2 | 5/2020 | McEwen et al. | |
| 2001/0000262 | A1 * | 4/2001 | McEwen ..... | A61H 9/0078 601/11 |
| 2002/0016610 | A1 | 2/2002 | Hovanes et al. | |
| 2003/0032905 | A1 | 2/2003 | Waldridge et al. | |
| 2003/0036771 | A1 | 2/2003 | McEwen et al. | |
| 2005/0070828 | A1 | 3/2005 | Hampson et al. | |
| 2005/0182331 | A1 | 8/2005 | Millay et al. | |
| 2006/0224181 | A1 * | 10/2006 | McEwen ..... | A61B 17/1355 606/202 |
| 2006/0253150 | A1 * | 11/2006 | McEwen ..... | A61B 5/02233 606/202 |
| 2007/0005106 | A1 | 1/2007 | Adducci | |
| 2007/0260148 | A1 * | 11/2007 | McEwen ..... | A61B 17/1355 600/490 |
| 2008/0262533 | A1 * | 10/2008 | McEwen ..... | A61B 17/1355 606/202 |
| 2009/0124912 | A1 * | 5/2009 | McEwen ..... | A61B 17/135 600/495 |
| 2010/0324429 | A1 * | 12/2010 | Leschinsky ..... | A61B 5/02208 600/493 |
| 2011/0034762 | A1 | 2/2011 | Pagonon | |
| 2011/0160022 | A1 | 6/2011 | Sato | |
| 2013/0138001 | A1 | 5/2013 | Wu | |
| 2013/0184745 | A1 * | 7/2013 | Leschinsky ..... | A61B 5/6831 606/202 |
| 2013/0211269 | A1 * | 8/2013 | Leschinsky ..... | A61B 5/02225 600/499 |
| 2013/0331716 | A1 | 12/2013 | Wawro et al. | |
| 2014/0142473 | A1 | 5/2014 | Lowe et al. | |
| 2014/0155708 | A1 | 6/2014 | Patersen et al. | |
| 2015/0150560 | A1 | 6/2015 | Sato | |
| 2015/0297933 | A1 | 10/2015 | Fukuta et al. | |
| 2015/0351969 | A1 | 12/2015 | Farrow et al. | |
| 2016/0193491 | A1 | 7/2016 | Sato | |
| 2016/0262971 | A1 | 9/2016 | Doron et al. | |
| 2017/0112504 | A1 | 4/2017 | McEwen et al. | |
| 2017/0224335 | A1 | 8/2017 | Weaner et al. | |
| 2017/0224357 | A1 | 8/2017 | Whalen et al. | |
| 2017/0325825 | A1 | 11/2017 | Bybordi | |
| 2018/0021210 | A1 | 1/2018 | Stray-Gundersen et al. | |
| 2018/0229064 | A1 | 8/2018 | Tagami | |
| 2018/0290005 | A1 | 10/2018 | Sato | |
| 2020/0297569 | A1 | 9/2020 | Angelo et al. | |

FOREIGN PATENT DOCUMENTS

| | | |
|---|---|---|
| EP | 2277606 | 1/2011 |
| JP | H1145709 | 2/1999 |
| JP | 2006516426 | 7/2006 |
| WO | WO2007/016772 | 2/2007 |
| WO | WO2009/128561 | 10/2009 |
| WO | WO2013/019991 | 2/2013 |
| WO | WO2014/027347 | 2/2014 |
| WO | WO2016/087123 | 6/2016 |
| WO | WO2017/139508 | 8/2017 |
| WO | WO2017/149690 | 8/2017 |
| WO | WO2018/069931 | 4/2018 |
| WO | WO2019/068147 | 4/2019 |

OTHER PUBLICATIONS

Examination Report for Australian Patent Application No. 2015292215, mailed May 1, 2019.

Extended Search Report for European Patent Application No. 15825397.1 (mailed Apr. 9, 2018), 8 pages.

International Preliminary Report on Patentability for PCT/CA2015/050458 (mailed Feb. 9, 2017).

International Search Report for PCT/CA2015/050458 (mailed Jul. 29, 2015).

International Search Report and Written Opinion from PCT Application No. PCT/US2021/013029, mailed Apr. 14, 2021.

International Search Report and Written Opinion from PCT Application No. PCT/US2020/015166, mailed Mar. 24, 2020.

"Limb Occlusion Pressure (LOP)". Tourniquets.org (2017) (downloaded May 3, 2022).

Office Action for Canadian Patent Application No. 2,952,270, mailed Feb. 23, 2021.

Office Action for Japanese Patent Application No. 2017-503853, mailed Feb. 5, 2019.

Office Action from the State Intellectual Property Office of the People's Republic of China for Chinese Patent Application No. 201580035619.9, mailed Oct. 31, 2018 (with English translation).

Smart Cuff Devices Offered By Smart Tools Plus, LLC at https://www.smarttoolsplus/com/ (downloaded May 3, 2022).

Written Opinion for PCT/CA2015/050458 (mailed Jul. 29, 2015).

Younger, Alastair S. E. et al., "Wide Contoured Thigh Cuffs and Automated Limb Occlusion Measurement Allow Lower Tourniquet Pressures," *Clinical Orthopedics and Related Research*, No. 428:286-293 (Nov. 2004).

Kerr, J. et al., "Personalizing Tourniquet Pressures—SBP-Based Estimation Methods are Unsafe, Unreliable, and Inconsistent," *The 42nd Conference of the Canadian Medical and Biological Engineering Society*, 4 pages (May 21-24, 2019).

* cited by examiner

TOURNIQUET SYSTEM FOR PERSONALIZED RESTRICTION OF BLOOD FLOW

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This is *a reissue of U.S. Pat. No. 10/646,232, issued May 12, 2020, which is* the U.S. National Stage of International Application No. PCT/CA2015/050458, filed May 20, 2015, which was published in English under PCT Article 21(2), which in turn claims the benefit of U.S. Provisional Application No. 62/029,288, filed Jul. 25, 2014. The provisional application is incorporated herein in its entirety.

FIELD OF THE INVENTION

This invention pertains to pneumatic tourniquet systems used for restricting the flow of arterial blood into a portion of a patient's limb to facilitate the safe performance of a physical activity while arterial blood flow is restricted to a limb involved in the activity. In particular, this invention pertains to a pneumatic tourniquet apparatus for establishing and maintaining a pressure to facilitate safe physical activity with personalized blood flow restriction for short time periods.

BACKGROUND

There is a need for a tourniquet system that can establish and maintain a personalized restrictive pressure (PRP) to facilitate safe physical activity for each patient for short periods of time, and that is optimized for each physical activity and for each applied tourniquet cuff. Preferably, such a system would be suitable for use without the need for substantially increased training, knowledge or skill There is a need for a personalized tourniquet system that can provide an indication of the intensity level, duration, and intervals, and repetition rates of the physical activity without the need for separate activity sensors. There is a related need for a safe tourniquet system that will prevent pressurization of the tourniquet cuff to a PRP for a time period that may be hazardous to the patient. There is a need for a system that can provide compliance monitoring for comparing and controlling sensed movement levels, sensed exercise intervals and sensed interval repetition rates to prescribed movement levels, prescribed exercise intervals, and prescribed interval repetition rates. There is a related need for a tourniquet system for personalized restriction of blood flow that has a dual-purpose tourniquet cuff wherein the same inflatable bladder of the tourniquet cuff can be separately operated as a patient sensor or as a tourniquet effector, or simultaneously operated as a combined sensor and effector.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
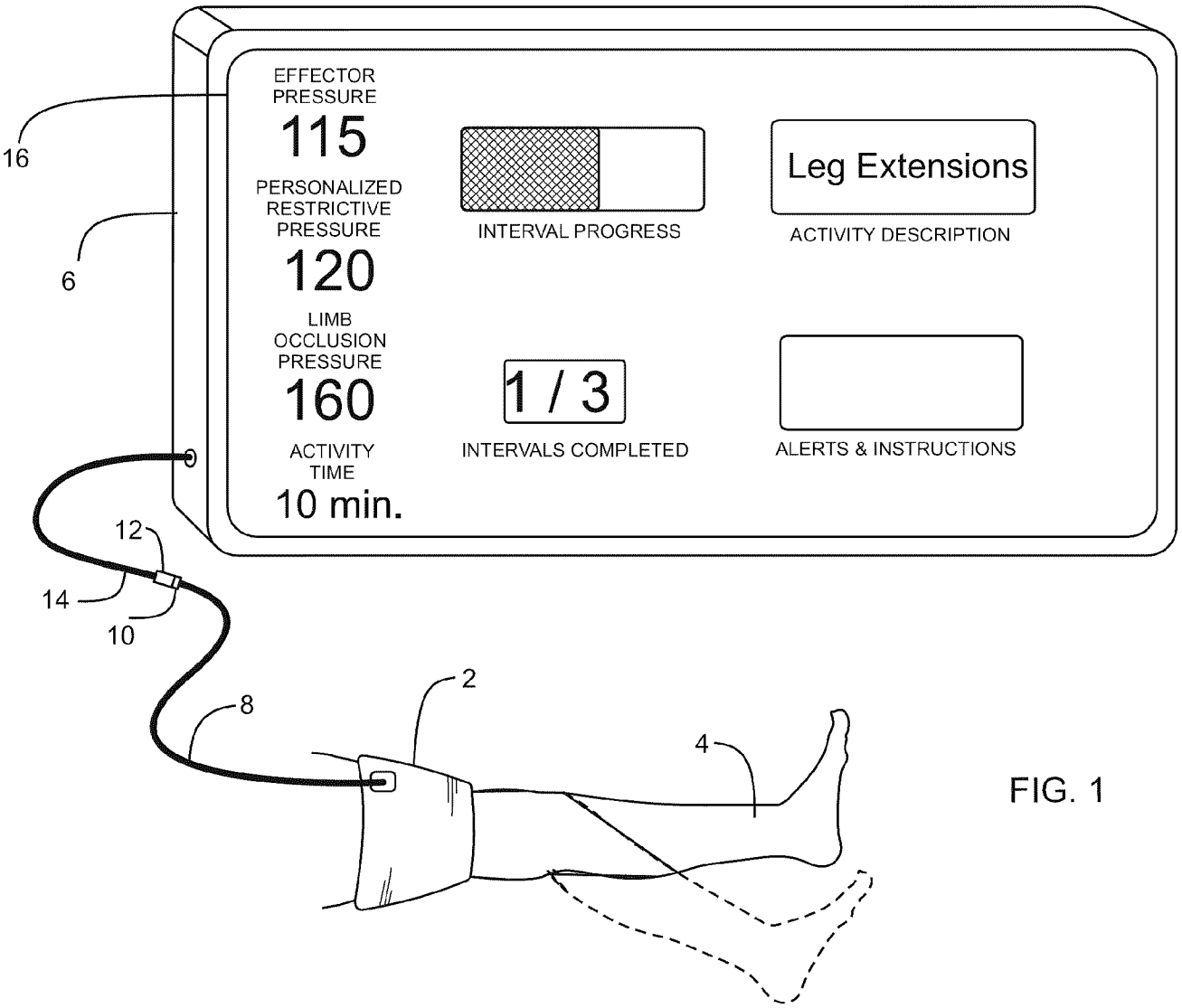
FIG. 1 is a pictorial representation of the preferred embodiment in use during blood flow restricted physical activity.

FIG. 1 depicts the tourniquet system of the preferred embodiment in typical use during a period of Blood Flow Restricted (BFR) physical activity (activity time period). BFR physical activity may be prescribed by a physician or physical therapist to strengthen and increase the mass of selected muscle groups by low load exercise.

Tourniquet cuff 2 is shown encircling a patient limb 4. Cuff 2 is a dual-purpose tourniquet cuff that effects the restriction of blood flow past the cuff when inflated and senses pneumatic pulsations in the cuff that enable instrument 6 to set a personalized restrictive pressure (PRP). PRP is a patient-specific safe level of pressure to be maintained in the inflatable bladder of cuff 2 for a limited period of time while the BFR activity is being performed. In the preferred embodiment PRP is determined automatically by instrument 6 prior to the commencement of the BFR activity in a pre-activity time period.

During the pre-activity time period, instrument 6 determines the Limb Occlusion Pressure (LOP), the minimum level of pressure required in the inflatable bladder of cuff 2 to stop arterial blood from penetrating past the region of limb 4 encircled by cuff 2, and uses the Limb Occlusion Pressure to establish a Personalized Restrictive Pressure (PRP) as described below. The Personalized Restrictive Pressure (PRP) is typically less than the Limb Occlusion Pressure (LOP) and thereby restricts but does not stop arterial blood flow or penetration past the region of the limb encircled by the cuff during BFR activity.

Cuff 2 is a type of tourniquet cuff that has common predetermined parameters that makes it suitable as a dual-purpose cuff including: a single inflatable bladder having a length sufficient to surround limb 4; a cuff width-to-circumference ratio between 0.15 to 0.4 which is substantially different than other types of cuffs such as those approved for blood pressure measurement; a continuous pneumatic passageway that pneumatically connects a cuff port 8 to all parts of the inflatable bladder; and construction, materials, fasteners and design that produce safe low-pressure gradients on limb 4 when cuff 2 is inflated to a level that restricts the flow of arterial blood past the cuff during periods of activity.

A pneumatic passageway between instrument 6 and cuff 2 is provided by cuff port 8, male locking connector 10, female locking connector 12 and flexible tubing 14. Cuff port 8 is fitted with a male locking connector 10 that mates to form a releasable pneumatic connection with female locking connector 12.

To permit instrument 6 to automatically determine if cuff 2 is acceptable for the dual purposes of sensing blood flow and effecting the restriction of blood flow past the cuff, male locking connector 10 includes indicia that identify the physical characteristics of cuff 2. In the preferred embodiment the indicia is a distinct color that identifies the distinct physical characteristics of cuff 2 to instrument 6 and to a user of the preferred embodiment.

Female locking connector 12 includes a sensor responsive to the color of connector 10 and communicates the detected color information to instrument 6 when male connector 10 is mated with connector 12 to form a pneumatic passageway. It will be appreciated that alternate methods of automatically identifying cuff 2 may be used, for example: incorporating RFID devices into cuff 2 or into connector 10, or configuring the shape of connectors 10 and 12 so that only dual-purpose cuffs are connectable to instrument 6.

Instrument 6 utilizes a graphical touchscreen user interface 16 to display information to the user and to permit the user to control the operation of the preferred embodiment.

A user of the preferred embodiment may initiate or confirm desired actions to be performed by instrument 6 by touching touchscreen 16 within the perimeter of a graphical icon representative of an action to be performed by instrument 6. For example: a user may: during the pre-activity time period select to operate cuff 2 as a patient sensor to estimate a Personalized Restrictive Pressure (PRP); during the activity time period select to operate cuff 2 as an effector to maintain a level of pressure near the estimated PRP in cuff 2; adjust the level of pressure maintained in cuff 2; initiate the pressurization of cuff 2; initiate the depressurization of cuff 2 to a pressure level near zero; set a time limit for a maximum safe activity time alarm; temporarily silence audible alarms; set parameters for activity protocols for the BFR activity (described further below), and set other operational parameters of instrument 6. A user may be selectively inhibited from initiating some actions when hazard conditions are detected. Some operations may require the user to complete confirmation steps prior to initiating the desired action.

Touchscreen user interface 16 also displays information pertaining to the operation of instrument 6 to the user. Touchscreen user interface 16 may selectively display any of the following information: the level of pressure within cuff 2 measured by instrument 6 (effector pressure); the pressure level to be maintained in cuff 2 when cuff 2 is inflated (personalized restrictive pressure); the calculated LOP (limb occlusion pressure) the length of time that cuff 2 has been inflated (activity time) pressure warning indicators; alarm reference "limits" or values; alarm messages describing detected alarm events; information related to the activity being performed (interval progress, intervals completed, activity description, alerts & instructions); and other information and instructions pertinent to the operation of instrument 6. To facilitate a clear and rapid understanding of the information presented to the user of instrument 6, alphanumeric text, graphic icons, and color may all be used to convey information.

In FIG. 1, touchscreen user interface 16 is depicted as forming part of instrument 6. Touchscreen user interface 16 may also be remote from instrument 6 and communicate wirelessly with instrument 6. For example, touchscreen interface 16 may be integrated into a Smartphone Application and communicate via Bluetooth or WiFi with instrument 6.

Figure 2:
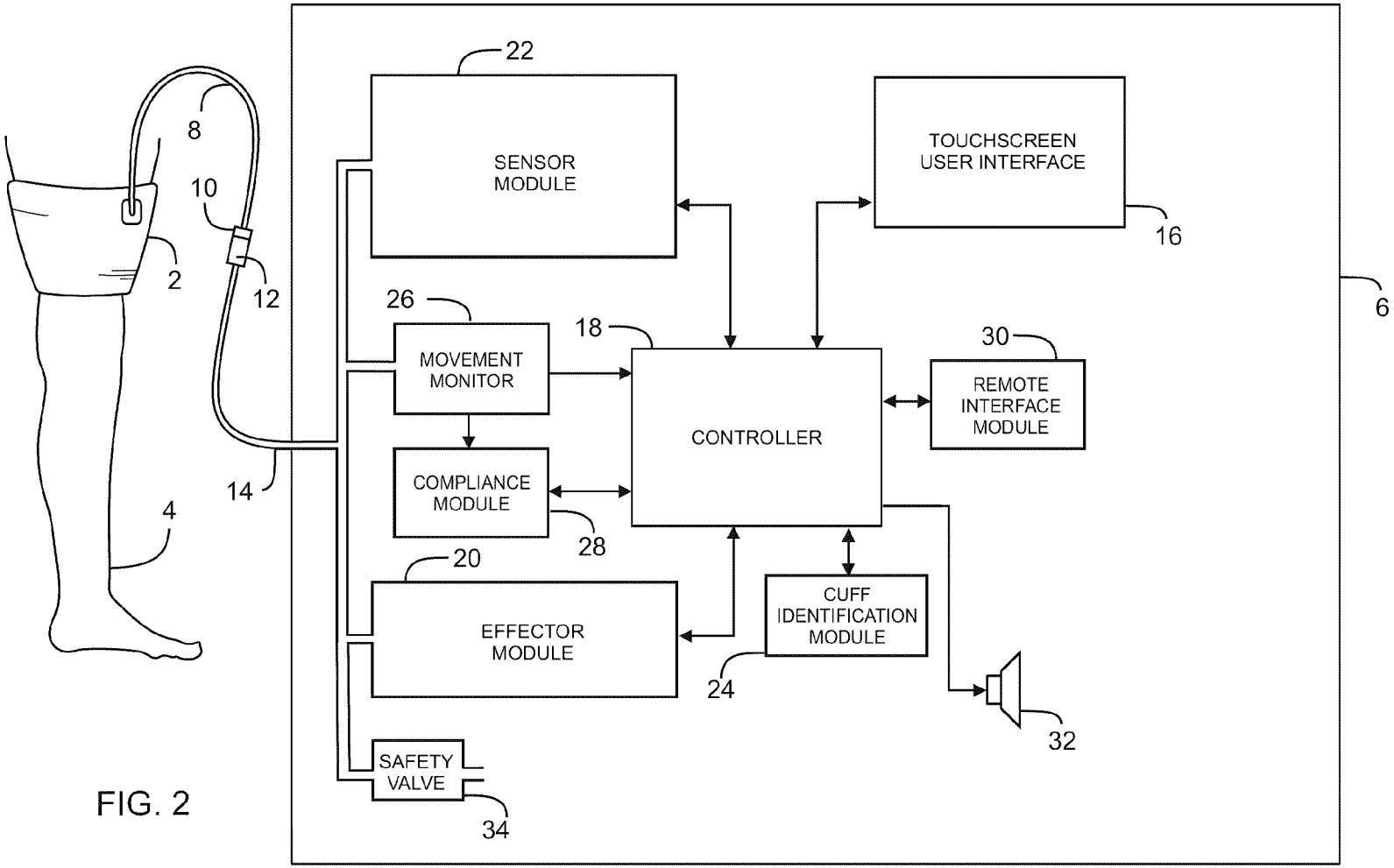
FIG. 2 is a block diagram of the preferred embodiment.

A block diagram of a preferred embodiment of instrument 6 is shown in FIG. 2. Referring to FIG. 2, controller 18 is a microcontroller typical of those known in the art with associated memory, analog, and digital peripheral interface circuitry, and other support components. Controller 18 executes software programs that control the operation of instrument 6 as described below. For clarity, and to enable a better understanding of the principles of the invention, some functions that are performed by controller 18 in conjunction with actuators and transducers are described and shown in FIG. 2 as separate functional blocks. These function blocks include effector module 20, sensor module 22, cuff identification module 24, movement monitor 26, compliance module 28, and remote interface module 30.

Touchscreen user interface 16 communicates with controller 18 to initiate actions and receive data for display. Touchscreen user interface 16 is similar to the touchscreen user interface described in U.S. Pat. App. No. 20130211445 and includes features to prevent hazards and suppress inadvertent and unintended actions.

Speaker 32 is used to alert a user of the preferred embodiment to alarm conditions. Speaker 32 is connected to controller 18. Electrical signals having different frequencies to specify different alarm signals and conditions are produced by controller 18 and converted to audible sound by speaker 32.

Safety valve 34 is a normally open valve that communicates pneumatically with the inflatable bladder of cuff 2. Safety valve 34 responds to an electrical control signal from controller 18 to close and open. It is used to prevent the bladder of cuff 2 from remaining pressurized for a hazardously long period of time, which may lead to patient injury. During the activity time period, the time that the pressure in the bladder is maintained near the PRP (activity time) is monitored and compared to a predetermined maximum safe activity time limit Upon reaching the maximum safe activity time limit, a hazard alert is produced by displaying an alarm message on touchscreen 16 and producing an audio tone through speaker 32, and controller 18 directs safety valve 34 to open and deflate the bladder of cuff 2 to a pressure near zero.

After the initiation of the activity time period, safety valve 34 remains closed at least until a predetermined minimum time limit has been exceed to provide time for cuff 2 to inflate to the PRP and the user to be notified via touchscreen 16 that the PRP has been reached.

Cuff identification module 24 communicates wirelessly with color sensors that form part of female connector 12. When cuff connector 10 is mated with connector 12, color sensors within connector 12 determine the color of connector 10. The color information from the sensors is communicated to cuff identification module 24.

Cuff identification module 24 maintains a data table that associates cuff connector color with predetermined physical characteristics of the connected cuff. The characteristics of the connected cuff are communicated to controller 18 and used by controller 18 as described further below. An example of a data table maintained by cuff identification module 24 is shown below in Table 1.

TABLE 1

| Connector Color | Dual-Purpose Cuff | Bladder Shape | Bladder Width | Bladder Length |
|---|---|---|---|---|
| Red | Yes | Curved | 3.25 in. | 18 in. |
| Green | Yes | Curved | 3.5 in. | 24 in. |
| Blue | Yes | Curved | 3.5 in. | 34 in. |
| Purple | Yes | Rectangular | 3.75 in. | 44 in. |
| White | No | Unknown | unknown | unknown |

If the type of cuff connected to instrument 6 is not a dual-purpose cuff, controller 18 alerts the user of instrument 6 by displaying a warning message on touchscreen 16 and configures touchscreen 16 to inhibit the selection of the cuff to operate as a sensor and effector. Touchscreen 16 may also be configured to permit a user to override the inhibited selection and permit the cuff to operate as an effector.

Figure 3:
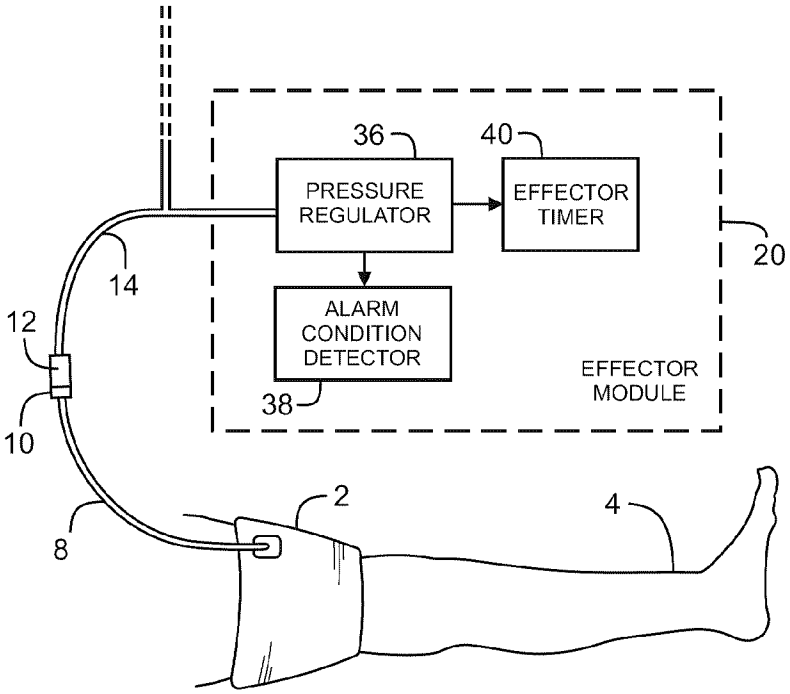
FIG. 3 is a detailed block diagram of the effector module.

Effector module 20 communicates with controller 18 and communicates pneumatically with the inflatable bladder of cuff 2. Effector module 20 is shown in detail in FIG. 3. Referring to FIG. 3, effector module 20 includes a pressure regulator 36, an alarm condition detector 38 and an effector timer 40. Pressure regulator 36 is an assemblage of components for regulating the pressure of air in the inflatable bladder of cuff 2 near a reference pressure level communicated from controller 18. Pressure regulator 36 is similar in design and operation to the tourniquet pressure regulator described in U.S. Pat. No. 8,083,763 and includes a combination of valves and a pressure source for maintaining the pressure level within the inflatable bladder of cuff 2 near a reference pressure level. Alternatively to reduce costs, a manually controllable pump and valve may be used in place of pressure regulator 36 to control pressure in cuff 2. In this case controller 18 would be configured to instruct the user via touchscreen user interface 16 to increase or decrease the pressure level for the purpose of estimating a LOP during a pre-activity time period, and maintaining pressure in the bladder of cuff 2 near the PRP during the activity time period.

During the activity time period when cuff 2 is inflated to restrict flow of arterial blood past cuff 2, alarm condition detector 38 monitors the operation of pressure regulator 36 and communicates signals indicative of detected alarm conditions to controller 18. Alarm conditions detected by alarm condition detector 38 are: occlusion of the pneumatic passageway between pressure regulator 36 and the inflatable bladder of cuff 2 (occlusion alarm); leakage from the inflatable bladder of cuff 2 or the pneumatic passageway between pressure regulator 36 and the inflatable bladder of cuff 2 (leak alarm); bladder pressure level too far below the desired reference pressure level (low pressure alarm); bladder pressure level too far above the desired reference pressure level (high pressure alarm); malfunction of pressure regulator 36 (malfunction alarm). It will be appreciated that other alarm conditions relevant to the operation of pressure regulator 36 may be detected by alarm condition detector 38.

Effector timer 40 operates to produce an indication of the length of time in minutes that the inflatable bladder of cuff 2 has been inflated (activity time). The activity time is communicated to controller 18 and displayed on touchscreen 16 when cuff 2 is operating as an effector to restrict arterial blood flow or penetration past cuff 2.

Referring to FIG. 2, sensor module 22 communicates pneumatically with the inflatable bladder of cuff 2 and communicates with controller 18. Sensor module 22 senses and analyzes pneumatic pulsations occurring in the inflatable bladder of cuff 2 to establish a Personalized Restrictive Pressure (PRP). The sensed pneumatic pulsations primarily arise from volume changes in the portion of the limb 4 encircled by cuff 2 that result from the flow of arterial blood into the limb 4 during each cardiac cycle.

Figure 4:
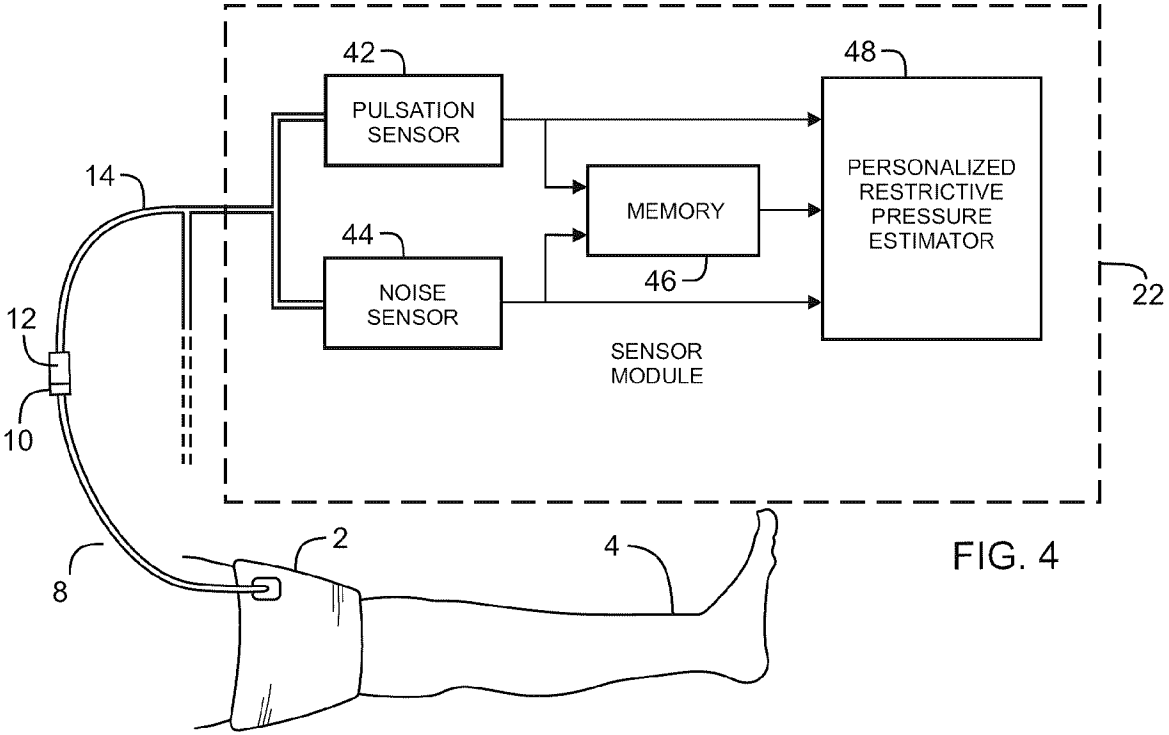
FIG. 4 is detailed block diagram of the sensor module.

Sensor module 22 is shown in detail in FIG. 4. Referring to FIG. 4, pulsation sensor 42 is shown in pneumatic communication with the inflatable bladder of cuff 2. Pulsation sensor 42 is optimized to detect and characterize pneumatic pulsations that are physiologic in origin and correspond to blood penetration into the region of the limb 4 encircled by cuff 2 occurring during each cardiac cycle. Levels of pulsation characteristics produced by sensor 42 that are indicative of blood penetration include maximum pulsation amplitude, pulsation area (integral over a cardiac cycle), and pulsation frequency spectrum. It will be appreciated that other pulsation characteristics may also be produced by sensor 42.

Sources of noise unique to the environment in which the preferred embodiment is used may produce pressure fluctuations in the bladder of cuff 2 that are independent of the pneumatic pulsations corresponding to the penetration of blood into the region of limb 4 encircled by cuff 2. Some of these noise sources can produce pressure fluctuations that mimic physiologic pulsations associated with blood penetration and affect the accuracy of the levels of pulsation characteristics produced by pulsation sensor 42. To characterize and quantify the level of noise present while physiologic pressure pulsations are being sensed by pulsation sensor 42 and to better discriminate between physiologic pressure pulsations and pressure fluctuations caused by noise sources and to help ensure accurate characterization of pulsations the preferred embodiment includes noise sensor 44. Noise sensor 44 communicates pneumatically with the bladder of cuff 2.

Information relating to the physical characteristics of cuff 2 from cuff identification module 24 may be used by physiologic pulsation sensor 42 and noise sensor 44 to better optimize the sensing of physiologic pulsations and to better determine levels of noise.

The levels of characteristics of each sensed physiologic pulsation are communicated to pulsation memory 46 and to personalized restrictive pressure estimator 48 by pulsation sensor 42. The level of noise associated with the sensed pulsation is also communicated to memory 46 and estimator 48 by noise sensor 44. If the level of noise associated with a sensed pulsation exceeds a predetermined threshold the levels of the pulsation's characteristics may be rejected by memory 46 and estimator 48. If the number of rejected pulsations exceed a predetermined alert limit within a predetermined alert time period, controller 18 acts to signal the user by displaying an alarm message on touchscreen 16 and producing an audio tone.

For a sensed pulsation, memory 46 records the levels of the pulsation's characteristics, the level of noise near the time the pulsation was sensed and the level of pressure in the bladder of cuff 2 near the time when the pulsation was sensed. Pulsation memory 46 may record the levels of pulsation characteristics and associated level of noise and associated level of pressure in the bladder of cuff 2 for one or more sensed pulsations depending on the operating mode of the preferred embodiment.

Estimates of LOP and PRP are made during the pre-activity time period. When a user initiates an estimate of LOP and PRP via touchscreen interface 16, controller 18 and sensor module 22 operate as follows:

a) Controller 18 directs the user to inflate the bladder of cuff 2 to a predetermined default pressure level chosen to stop the flow of blood past the region of limb 4 encircled by cuff 2. In the preferred embodiment the predetermined default pressure level is 300 mmHg. It will be appreciated that other default pressure levels may be predetermined and that the default pressure level may be dependent upon characteristics of the cuff connected to instrument 6 as reported by cuff identification module 24. A default pressure level may also be selected by a user of instrument 6 via touchscreen user interface 16.

b) The levels of characteristics of detected physiologic pulsations associated with the default level of pressure in the bladder of cuff 2 are recorded in pulsation memory 46. The level of noise associated with the detected pulsations is also recorded in pulsation memory 46.

c) Controller 18 then directs effector module 20 to decrease the level of pressure in the bladder of cuff 2 by predetermined increments until a predetermined minimum level of pressure is reached. Following each decrease in the level of pressure in the bladder of cuff 2, the levels of characteristics of detected physiologic pulsations, their associated level of noise and associated level of pressure are recorded in memory 46. When the predetermined minimum level of pressure has been reached controller 18 directs effector module 20 to deflate the bladder.

d) Estimator 48 then retrieves the levels of pulsation characteristics and their associated bladder pressure levels from memory 46. Estimator 48 compares and analyzes the recorded levels of characteristics to determine the maximum levels of pulsation characteristics recorded while the level of pressure in the bladder of cuff 2 was being decreased. Generally, as the level of pressure in the bladder of cuff 2 is decreased the distance of penetration of blood into the region of the limb 4 encircled by cuff 2 increases and the levels of characteristics of physiologic pulsations also increase. The levels of characteristics of physiologic pulsations are at their maximum levels when the level of pressure in the bladder of cuff 2 is at a pressure that is below LOP and arterial blood is flowing past the region of limb 4 encircled by cuff 2. Levels of characteristics of pulsations associated with LOP have been found to have a predetermined relationship with the maximum levels of pulsation characteristics that are detected when blood is flowing past the cuff 2.

e) After determining the maximum levels of pulsation characteristics recorded while the level of pressure in the bladder of cuff 2 was decreased from a default level of pressure to a predetermined minimum level of pressure, estimator 48 computes, using predetermined percentages of the maximum levels, the levels of pulsation characteristics that will match the levels of pulsation characteristics detected when the level of pressure in the bladder of cuff 2 is near the LOP.

f) Estimator 48 analyzes the recorded levels of pulsation characteristics and their associated levels of pressure to estimate the patient's LOP by calculating the level of pressure required in the bladder of cuff 2 to produce pulsations with characteristics that match the previously computed levels of pulsation characteristics associated with LOP. Estimator 48 also analyzes the recorded levels of noise associated with the pulsation characteristics to determine the level of noise associated with the LOP estimation. To compensate for any effects that noise may have on the accuracy of the LOP estimation, estimator 48 uses the estimated LOP and the level of noise associated with the LOP estimation to determine the estimated PRP. The estimated PRP computed by estimator 48 is a function of the estimated LOP and the level of noise associated with the LOP estimation. If the level of noise associated with the LOP estimation is greater than or equal to a noise threshold, the estimated LOP is increased by a predetermined pressure increment to compensate for error that may have been introduced by the noise. PRP is then established as a predetermined percentage of the LOP. This predetermined percentage is typically less than 100% resulting in a PRP that is less than LOP. The predetermined percentage may also be a user selected value below, equal to, or above 100% of the LOP. Percentages above 100% result in a PRP that stops the penetration of blood past the region of the limb encircled by the cuff.

It will be appreciated that other functions of estimated LOP and associated noise levels may be used to estimate a PRP other than the functions described above.

Estimator 48 may be configured alternatively to determine a PRP by using a predetermined percentage of a pulsation characteristic associated with LOP to establish a PRP instead of using a predetermined percentage of the LOP itself. In this configuration, estimator 48 determines an LOP by either sensing a characteristic of blood that penetrates past the applied tourniquet cuff 2 or as described above by using characteristics of pulsations sensed in the inflatable bladder of cuff 2 at various pressures. After estimator 48 determines LOP, controller 18 directs effector module 20 to pressurize the cuff to the LOP to allow pulsation sensor 42 to sense levels of pulsation characteristics, such as maximum pulsation amplitude and pulsation area, at the LOP. Estimator 48 then finds the pressure corresponding to a level of pulsation characteristic that is a predetermined percentage of the level of that pulsation characteristic at LOP and sets this pressure as the PRP. The predetermined percentage used to determine the desired pulsation characteristic at the PRP may be a function of the magnitude of the LOP, for example if the LOP was 120 mmHg the predetermined percentage may be 70% and if the LOP was 150 mmHg the predetermined percentage may be 80%.

Estimator 48 may also be configured to estimate PRP directly without first estimating LOP, using the levels of pulsation characteristics recorded while the level of pressure in the bladder of cuff 2 was decreased from a default level of pressure to a predetermined minimum level of pressure. In this case, estimator 48 retrieves the recorded levels of pulsation characteristics and their associated bladder pressure levels from memory 48 and compares and analyzes the recorded levels of characteristics to determine the maximum levels of pulsation characteristics recorded while the level of pressure in the bladder of cuff 2 was being decreased. Estimator 48 then finds the pressure corresponding to a level of pulsation characteristic that is a predetermined percentage of the maximum stored level of that pulsation characteristic and sets this pressure as the PRP.

It will be apparent that to record the levels of pulsation characteristics associated with varying levels of pressure in the bladder of cuff 2 between a default pressure and a minimum pressure, a sequence other than that described above (where the level of pressure is reduced in predetermined amounts from a default level to a minimum level) may be used. For example: controller 18 may direct effector module 20 to inflate the bladder of cuff 2 to a predetermined minimum level and increase the level of pressure in predetermined increments until a default pressure level is reached; controller 18 may also vary the predetermined increment amount, default level of pressure and minimum level of pressure in response to the magnitude of the levels of physiologic pulsation characteristics detected and their associated level of pressure in the bladder of cuff 2.

Figure 5A:
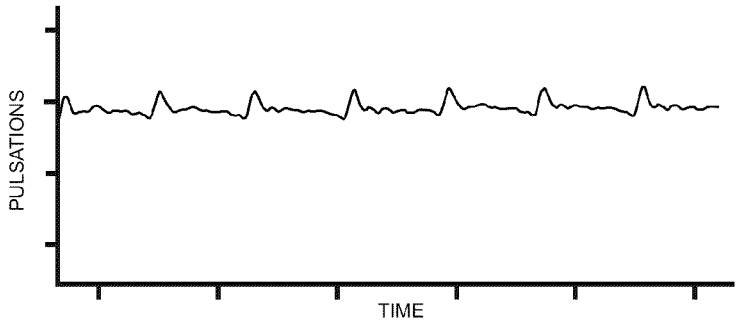
FIGS. 5a, 5b, and 5c are graphs of pneumatic pressure fluctuations sensed by the dual-purpose cuff
Figure 5B:
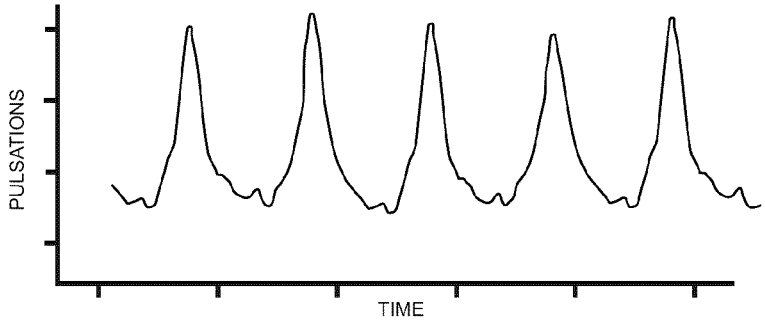
Figure 5C:
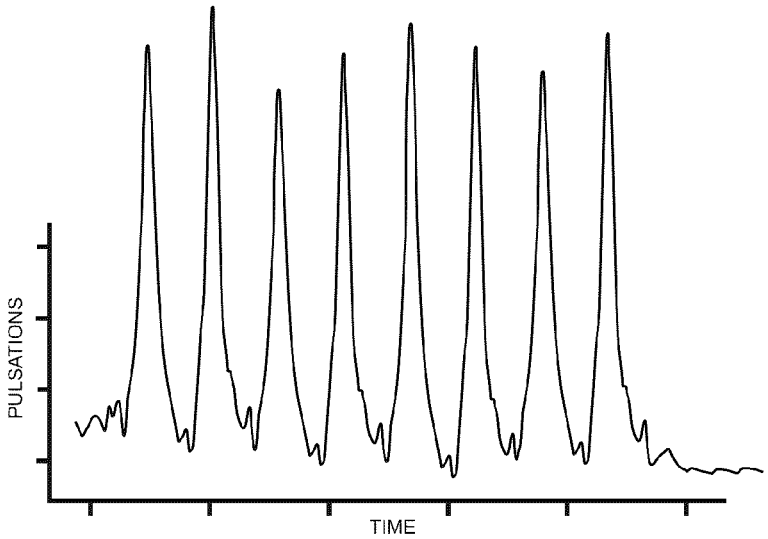

Referring to FIG. 2, movement monitor 26 communicates pneumatically with the inflatable bladder of cuff 2 and communicates with controller 18 and compliance module 28. Movement monitor 26 senses and analyzes pneumatic pressure fluctuations occurring in the inflatable bladder of cuff 2 which are indicative of movement of limb 4 to which cuff 2 is applied. Based on the amplitude and frequency of the pressure fluctuations, movement monitor 26 determines the level of movement and duration of movement during the activity time period. FIG. 5a shows pressure fluctuations occurring in cuff 2 when limb 4 is stationary. FIG. 5b shows pressure fluctuations occurring in cuff 2 in response to low intensity and low repetition rate movements of limb 4. FIG. 5c shows pressure fluctuations occurring in cuff 2 in response to high intensity and high repetition rate movements of limb 4. In FIGS. 5b and 5c each pressure fluctuation corresponds to a single movement of the limb performing the activity, thus the plurality of fluctuations shown in these plots is indicative of multiple repetitions of the movement being performed by the limb.

A patient for which BFR physical activity has been prescribed is also typically prescribed an activity protocol specific to their needs consisting of movement levels (intensity of movement during the activity), exercise intervals (time interval during which activity should take place), interval repetition rates (number of exercise intervals to take place) and a maximum safe activity time limit. In prescribing a protocol a therapist sets limits for movement levels, exercise intervals, interval repetition rates and a maximum safe activity time, which are communicated to a compliance module 28. Compliance module 28 is included in the preferred embodiment for the purpose of monitoring patient compliance with the prescribed activity protocol. The benefit of prescribing activity protocols and monitoring patient compliance to the protocols is that patient outcomes can be evaluated with respect to the activities actually performed by the patient. During the activity time period, the movement level and duration determined by movement monitor 26 is communicated to the compliance module 28 where it is compared to the limits set by the therapist for the prescribed activity protocol. If the movement takes place throughout the prescribed exercise interval a compliance alert is produced to indicate completion of the interval. If the movement level is too high or too low, or if the duration of movements is not in conformance to the exercise interval (i.e. insufficient movements within an exercise interval or movements detected outside the exercise interval), or if movements don't take place at all within one of the prescribed exercise intervals, alerts are produced by the compliance module 28 and communicated to the therapist. In addition to the above described aspects of an activity protocol (movement levels, exercise intervals, and interval repetition rates), the predetermined percentage of LOP used to establish the PRP may be defined in the compliance module and communicated to the sensor module 22 via controller 18. This enables individual percentages to be specified by a user for each exercise interval or for the BFR activity as a whole.

Instrument 6 communicates with remote devices via remote interface module 30. Remote interface module 30 provides the physical communication interface such as USB, Ethernet, Bluetooth or WiFi and the appropriate communication protocol specific to the connected remote device. Data that may be reported or received from a remote device includes: data and events from the pre-activity time period such as the measurement of the LOP and PRP, cuff pressure level settings, alarm limit settings, and activity protocol parameters; and data and events from the activity time period such as alarm conditions, exercise intervals completed, activity time, cuff pressure levels, adjustments to pressure level settings and alarm limit settings, and compliance alerts or other alerts.

For example, the touchscreen user interface 16 may be physically separated from instrument 6 and communicate wirelessly with instrument 6 via remote interface module 30. Additionally, remote interface module 30 provides a communication link for a device such as a remote compliance monitor, which enables a therapist to remotely communicate with compliance module 28 for the purpose of prescribing parameters for activity protocols and monitoring patient compliance to the protocols. To ensure patient safety, if communication is lost between instrument 6 and a remote device essential to the function of the instrument 6 such as a remote touchscreen user interface, controller 18 will direct safety valve 34 to deflate cuff 2 and inhibit re-inflation until the communication is re-established. If communication is lost between instrument 6 and a remote device for monitoring patient compliance such as a remote compliance monitor, a communication alert would be produced by instrument 6 by displaying an alarm message on touchscreen 16 and producing an audio tone through speaker 32.

To permit a better understanding of how the preferred embodiment operates to enable BFR activity the following example is provided: Using a remote compliance monitor a therapist communicates via remote interface module 30 to compliance module 28 specific parameters pertaining to a desired BFR activity. The therapist sets the PRP to be a pressure that is 80% of the measured LOP, sets an upper and lower limit for the movement level, sets three 2 minute exercise intervals, and a maximum activity time limit of 10 minutes. Additionally the therapist sets the activity to be a leg extension exercise. Next, during the pre-activity time period, the patient using the preferred embodiment selects a suitable dual-purpose tourniquet cuff 2 to encircle the limb. The patient secures the cuff 2 around the limb 4 and connects it so that the cuff communicates pneumatically with instrument 6. Cuff identification module 24 attempts to identify the cuff 2 to determine if it is an acceptable dual-purpose tourniquet cuff. If the cuff 2 is not an acceptable dual-purpose cuff for use with the preferred embodiment or it cannot be identified a warning is given to the patient via touchscreen user interface 16 and the controls employed to initiate an estimate of PRP and to inflate the cuff are disabled, thereby preventing the use of an unacceptable cuff.

If the pneumatically connected cuff is acceptable a patient may initiate an estimate of personalized restrictive pressure (PRP) by touching a corresponding graphic icon shown on touchscreen user interface 16.

To estimate the PRP, instrument 6 will inflate the bladder of cuff 2 to various levels while recording the levels of characteristics of pneumatic physiologic pulsations associated with the pressure levels as described above. If during the estimation of PRP, noise that is independent of the pressure pulsations analyzed for the estimation of LOP is present, such as noise created by patient limb movement or regulation of the tourniquet instrument 6, and that noise exceeds a predetermined threshold, the estimation will be suspended and a warning message displayed touchscreen 16.

When instrument 6 has completed an estimation of LOP, the PRP is calculated to be 80% of the LOP and the PRP and LOP are displayed on touchscreen 16. The patient may then select the estimated PRP as the level of pressure to maintain in the bladder of cuff 2 during the activity time period. To ensure that the estimated PRP remains relevant to the physiologic state of the patient, controller 18 only permits a patient to select the estimated PRP as the level of pressure to be maintained in the bladder of cuff 2 during the activity for a predetermined period of time after the estimation of PRP has been completed. If the PRP is not selected within the predetermined period of time another estimate of PRP must be initiated or the patient must select a default pressure level to be maintained in the bladder of cuff 2 during the activity time period.

After selecting the level of pressure to be maintained in the bladder of cuff 2 during the activity time period, the patient may initiate the tourniquet effector (inflate cuff 2) by touching an icon on touchscreen 16.

Once the tourniquet effector is initiated and the bladder is inflated to the PRP, the activity time period begins. During this time period, the patient commences the leg extension exercise for the first 2 minute exercise interval. As the patient performs the movement, movement monitor 26 senses pressure fluctuations in the bladder and determines a level of movement of the limb associated with the pressure fluctuations. If, during the exercise interval, the level of movement is less than the predetermined minimum, an inactivity alert is produced. Conversely, if the level of movement is greater than the predetermined maximum, an overactivity alert is produced. If the patient stops the movement partway through the 2 minute interval or tries to continue the movement beyond the 2 minute interval a compliance alert is produced by the compliance module 28. Once the first 2 minute interval is completed a compliance alert is produced by the compliance module 28 and the patient ceases movement until the beginning of the next exercise interval. The patient repeats the same BFR exercise interval two more times within the 10 minute maximum activity time limit Additional alerts are produced if the patient does not perform the movement at all during the specified exercise interval, or tries to perform the movement at a time within the 10 minute activity time limit outside the three exercise intervals specified by the therapist.

After the patient completes the specified number of intervals, the touchscreen user interface 16 directs the patient to deflate the cuff 2. If the patient does not deflate the cuff 2 and the cuff 2 remains inflated until the 10 minute maximum safe activity time limit is reached, controller 18 automatically directs safety valve 34 to deflate the bladder of the tourniquet cuff 2.

Compliance module 28 communicates to the patient, via touchscreen 18 and to remote compliance monitor connected via remote interface module 30, a summary of the activity performed during the activity time period including exercise intervals completed, and any compliance alerts or activity alerts.

The invention claimed is:

1. Apparatus for personalized restriction of blood flow into a limb and penetration past a tourniquet cuff based on a personalized restrictive pressure (PRP), comprising:

a dual-purpose tourniquet cuff having a single inflatable bladder adapted to encircle a limb;

*a controller selectively operating the inflatable bladder of the dual-purpose tourniquet cuff and executing instruction to control:* a sensor module having a pulsation sensor communicating pneumatically with the inflatable bladder of the dual-purpose *tourniquet* cuff for measuring pressure pulsations to characterize a limb occlusion pressure (LOP), thereby to identify a minimum pressure at which arterial blood penetration past the cuff is stopped;

a PRP estimator responsive to the sensor module for producing an estimate of a PRP, wherein the estimate of the PRP is less than the LOP and indicative of a level of pressure in the inflatable bladder that restricts but does not stop arterial blood penetration past the cuff; *and* an effector module communicating pneumatically with the inflatable bladder of the dual-purpose *tourniquet* cuff for maintaining pressure in the *inflatable* bladder near the PRP, thereby restricting but not stopping arterial blood penetration past the cuff[; and a controller selectively operating the inflatable bladder in conjunction with the sensor module and the effector module].

2. The apparatus of claim 1 wherein the controller operates the inflatable bladder with the sensor module during a pre-activity time period.

3. The apparatus of claim 1 wherein the controller operates the inflatable bladder with the effector module during an activity time period.

4. The apparatus of claim 3 wherein the controller further operates the inflatable bladder with a movement monitor for measuring pressure fluctuations indicative of movement of the limb during the activity time period.

5. The apparatus of claim 1 and including an alarm condition detector producing an alert upon detection of an occlusion of pneumatic communication between the inflatable bladder and the sensor module.

6. The apparatus of claim 1 and including an alarm condition detector producing an alert upon detection of an occlusion of pneumatic communication between the inflatable bladder and the effector module.

7. The apparatus of claim 1 and including a cuff identification module for alerting a user in instances when the inflatable bladder is not part of a dual-purpose cuff.

8. The apparatus of claim 1, wherein measuring pressure pulsations to characterize a limb occlusion pressure (LOP) comprises determining the pressure required in the dual-purpose *tourniquet* cuff to produce characteristics that match previously computed levels of pulsation characteristics associated with LOP.

9. An apparatus for regulating tourniquet cuff pressure based on a personalized restrictive pressure (PRP), comprising:

a dual-purpose tourniquet cuff having a single inflatable bladder and configured to be applied to a location on a limb;

*a controller operable during an activity time period for maintaining pressure in the dual-purpose tourniquet cuff near the PRP, thereby restricting but not stopping arterial blood penetration past the dual-purpose tourniquet cuff during the activity time period, the controller executing instructions to control:*

*a sensor module having a pulsation sensor communicating pneumatically with the inflatable bladder of the dual-purpose tourniquet cuff for measuring pressure pulsations to characterize a limb occlusion pressure (LOP), the sensor module having;* an estimating component operable to estimate a limb occlusion pressure (LOP) by determining a minimum pressure in the *inflatable* bladder at which arterial blood penetration past the dual-purpose tourniquet cuff is stopped; *and* an establishing component operable to establish a PRP by determining a second pressure that is less than the LOP[; and a control component operable during an activity time period for maintaining pressure in the dual-purpose tourniquet cuff near the PRP, thereby restricting but not stopping arterial blood penetration past the dual-purpose cuff during the activity time period].

[10. An apparatus for regulating tourniquet cuff pressure based on a personalized restrictive pressure (PRP), comprising:

a dual-purpose tourniquet cuff having a bladder and configured to be applied to a location on a limb;

control means operable during a pre-activity time period for estimating a pressure at which arterial blood penetration past the dual-purpose tourniquet cuff is restricted but not stopped by analyzing pressure pulsations in the bladder of the cuff that are associated with selected pressures in the bladder, thereby to identify a PRP at the location;

regulation means operable during an activity time period for maintaining pressure in the bladder of the dual-purpose tourniquet cuff near the PRP, thereby restricting but not stopping arterial blood penetration past the cuff during the activity time period; and movement sending means for determining a level of movement of the limb associated with pressure fluctuations in the bladder that are independent of the pressure pulsations analyzed for the estimation of the PRP.]

[11. The apparatus of claim 10 including sensing means for determining a noise level associated with pressure fluctuations in the bladder that are independent of the pressure pulsations analyzed for the estimation of the PRP.]

[12. The apparatus of claim 11 further comprising alert means for producing an alert perceptible by a user if the noise level is greater than a threshold level.]

[13. The apparatus of claim 10 and including a cuff identification means for alerting a user in instances when the inflatable bladder is not part of a dual-purpose cuff.]

*14. An apparatus for personalized restriction of blood flow into a limb and penetration past a tourniquet cuff based on a personalized restrictive pressure (PRP), comprising:*

*a dual-purpose tourniquet cuff having a single inflatable bladder adapted to encircle a limb;*

*a controller selectively operating the inflatable bladder of the dual-purpose tourniquet cuff, the controller executing instructions to control:*

*a sensor module having a pulsation sensor communicating pneumatically with the inflatable bladder of the dual-purpose tourniquet cuff for measuring pressure pulsations to characterize a limb occlusion pressure (LOP), thereby to identify a minimum pressure at which arterial blood penetration past the cuff is stopped; and*

*a PRP estimator responsive to the sensor module for producing an estimate of a PRP, wherein the estimate of the PRP is less than the LOP and indicative of a level of pressure in the inflatable bladder that restricts but does not stop arterial blood penetration past the cuff.*

*15. An apparatus for personalized restriction of blood flow into a limb and penetration past a tourniquet cuff based on a personalized restrictive pressure (PRP), comprising:*

*a dual-purpose tourniquet cuff having a single inflatable bladder adapted to encircle a limb;*

*a controller comprising a microcontroller, the controller selectively operating the inflatable bladder of the dual-purpose tourniquet cuff, the controller executing instructions to control:*

*a sensor module having a pulsation sensor communicating pneumatically with the inflatable bladder of the dual-purpose tourniquet cuff for measuring pressure pulsations to characterize a limb occlusion pressure (LOP), thereby to identify a minimum pressure at which arterial blood penetration past the cuff is stopped;*

*a PRP estimator responsive to the sensor module for producing an estimate of a PRP, wherein the estimate of the PRP is less than the LOP and indicative of a level of pressure in the inflatable bladder that restricts but does not stop arterial blood penetration past the cuff; and*

*an effector module communicating pneumatically with the inflatable bladder of the dual-purpose tourniquet cuff for inflating the inflatable bladder to a pressure near the PRP, thereby restricting but not stopping arterial blood penetration past the cuff.*

*16. An apparatus for personalized restriction of blood flow into a limb and penetration past a tourniquet cuff based on a personalized restrictive pressure (PRP), comprising:*

*a dual-purpose tourniquet cuff having a single inflatable bladder adapted to encircle a limb;*

*a controller selectively operating the inflatable bladder of the dual-purpose tourniquet cuff, the controller executing instructions to control:*

*a sensor module having a pulsation sensor communicating pneumatically with the inflatable bladder of the dual-purpose tourniquet cuff for measuring pressure pulsations to characterize a limb occlusion pressure (LOP), thereby to identify a minimum pressure at which arterial blood penetration past the cuff is stopped;*

*a PRP estimator responsive to the sensor module for producing an estimate of a PRP, wherein the estimate of the PRP is less than the LOP and indicative of a level of pressure in the inflatable bladder that restricts but does not stop arterial blood penetration past the cuff; and*

*an effector module communicating pneumatically with the inflatable bladder of the dual-purpose tourniquet cuff for setting a pressure in the inflatable bladder near the PRP, thereby restricting but not stopping arterial blood penetration past the cuff.*

*17. An apparatus for setting tourniquet cuff pressure based on a personalized restrictive pressure (PRP), comprising:*

*a dual-purpose tourniquet cuff having a single inflatable bladder and configured to be applied to a location on a limb;*

*a controller selectively operating the inflatable bladder of the dual-purpose tourniquet cuff, the controller operable for setting pressure in the dual-purpose tourniquet cuff near the PRP, thereby restricting but not stopping arterial blood penetration past the dual-purpose tourniquet cuff, the controller executing instructions to control:*

*a sensor module having a pulsation sensor communicating pneumatically with the inflatable bladder of the dual-purpose tourniquet cuff to characterize a limb occlusion pressure (LOP), the sensor module having;*

*an estimating component operable to estimate a limb occlusion pressure (LOP) by determining a minimum pressure in the inflatable bladder at which arterial blood penetration past the dual-purpose tourniquet cuff is stopped; and*

*an establishing component operable to establish a PRP by determining a second pressure that is less than the LOP.*

*18. An apparatus for pressurizing a tourniquet cuff based on a personalized restrictive pressure (PRP), comprising:*

*a dual-purpose tourniquet cuff having a single inflatable bladder and configured to be applied to a location on a limb;*

*a controller selectively operating the inflatable bladder of the dual-purpose tourniquet cuff, the controller executing instructions to control:*

*a sensor module having a pulsation sensor communicating pneumatically with the inflatable bladder of*

*the dual-purpose tourniquet cuff to characterize a limb occlusion pressure (LOP), the sensor module having:*

*an estimating component operable to estimate a limb occlusion pressure (LOP) by determining a minimum pressure in the inflatable bladder at which arterial blood penetration past the dual-purpose tourniquet cuff is stopped;*

*an establishing component operable to establish a PRP by determining a second pressure that is less than the LOP; and*

*a pressurizing component operable for pressurizing the dual-purpose tourniquet cuff to a pressure near the PRP, thereby restricting but not stopping arterial blood penetration past the dual-purpose tourniquet cuff.*

* * * * *